US00PP13974P29

(12) United States Plant Patent
Smith

(10) Patent No.: US PP13,974 P2
(45) Date of Patent: Jul. 15, 2003

(54) CHRYSANTHEMUM PLANT NAMED 'REGAL YOCHERYL'

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/094,275

(22) Filed: Mar. 8, 2002

(51) Int. Cl.[7] ..... A01H 5/00

(52) U.S. Cl. ..... Plt./292

(58) Field of Search ..... Plt./292, 287, 291

*Primary Examiner*—Bruce R. Campell
*Assistant Examiner*—A H Para
(74) *Attorney, Agent, or Firm*—C. A. Whealy

(57) ABSTRACT

A distinct cultivar of Chrysanthemum plant named 'Regal Yocheryl', characterized by its upright and mounded plant habit; freely branching habit; uniform and freely flowering habit; decorative-type inflorescences; purple-colored ray florets; and natural season flowering in early to mid-October in the Northern Hemisphere.

1 Drawing Sheet

BOTANICAL CLASSIFICATION/CULTIVAR DESIGNATION

*Chrysanthemum×morifolium* cultivar Regal Yocheryl.

BACKGROUND OF THE INVENTION

The present invention relates to a new and distinct cultivar of Chrysanthemum plant, botanically known as *Chrysanthemum×morifolium*, commercially known as a garden-type Chrysanthemum and hereinafter referred to by the name 'Regal Yocheryl'.

The new cultivar is a product of a mutation induction program conducted by the Inventor in Fort Myers, Fla. The objective of the breeding program is to create new garden-type Chrysanthemum cultivars having inflorescences with desirable inflorescence forms, attractive floret colors and good garden performance.

The new Chrysanthemum originated by exposing unrooted cuttings of the Chrysanthemum cultivar Yocheryl, disclosed in U.S. Plant Pat. No. 11,846, to X-ray radiation in July, 1998 in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Fort Myers, Fla. The new Chrysanthemum was discovered and selected by the Inventor as a single flowering plant within this population in January, 1999. The selection of this plant was based on its desirable inflorescence form, attractive ray floret color and good garden performance.

Asexual reproduction of the new cultivar by terminal cuttings taken in a controlled environment in Fort Myers, Fla. since March, 1999, has shown that the unique features of this new Chrysanthemum are stable and reproduced true to type in successive generations.

SUMMARY OF THE INVENTION

The cultivar Regal Yocheryl has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Regal Yocheryl'. These characteristics in combination distinguish 'Regal Yocheryl' as a new and distinct cultivar:

1. Upright and mounded plant habit.
2. Freely branching habit; dense and full plants.
3. Uniform and freely flowering habit.
4. Decorative-type inflorescences.
5. Purple-colored ray florets.
6. Natural season flowering in early to mid-October in the Northern Hemisphere.

Plants of the new Chrysanthemum are most similar to plants of the the cultivar Yocheryl. In side-by-side comparisons conducted in Fort Myers, Fla., plants of the new Chrysanthemum differed from plants of the cultivar Yocheryl in the following characteristics:

1. Ray florets of the new Chrysanthemum were darker purple than ray florets of the cultivar Yocheryl.
2. Ray florets of the new Chrysanthemum faded less than ray florets of the cultivar Yocheryl.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Regal Yocheryl'.

The photograph at the bottom of the sheet comprises a close-up view of typical inflorescences of the cultivar 'Regal Yocheryl'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Pendleton, S.C., under natural season conditions and practices which approximate those generally used in commercial garden-type Chrysanthemum production. One rooted cutting was planted in a 16.5-cm container in late July, 2002. Plants were not pinched, that is, the terminal apex was not removed to enhance branching. During the production of the plants, day temperatures ranged from 29 to 32° C. and night temperatures ranged from 16 to 21° C. Measurements and numerical values represent averages for typical flowering plants.

Botanical classification: *Chrysanthemum×morifolium* cultivar Regal Yocheryl.

Commercial classification: Decorative-type garden Chrysanthemum.

Parentage: Induced mutation of the *Chrysanthemum×morifolium* cultivar Yocheryl, disclosed in U.S. Plant Pat. No. 11,846.

Propagation:

*Type.*—Terminal tip cuttings.

*Time to initiate roots.*—About four days at 21° C.

*Time to produce a rooted cutting.*—About ten days at 21° C.

*Root description.*—White, fine and fibrous.

*Rooting habit.*—Freely branching.

Plant description:

*Appearance.*—Perennial herbaceous decorative-type garden Chrysanthemum. Inverted triangle. Stems initially upright, then somewhat outwardly spreading giving a uniformly mounded appearance to the plant. Freely branching with lateral branches forming at every node.

*Plant height.*—About 22 cm.

*Plant diameter.*—About 35.5 cm.

*Lateral branches.*—Length: About 18 cm. Diameter: About 5.5 mm. Internode length: About 1.3 cm. Aspect: Upright and outwardly spreading. Texture: Pubescent. Color: 146A.

*Foliage description.*—Leaf arrangement: Alternate. Length: About 4.6 cm. Width: About 3.2 cm. Apex: Cuspidate to mucronate. Base: Attenuate to truncate. Margin: Palmately lobed, sinuses mostly divergent. Texture: Both surfaces, pubescent; veins prominent on lower surface. Color: Young foliage upper surface: Darker than 147A. Young foliage lower surface: Darker than 147B. Mature foliage upper surface: Slightly darker than 147A. Mature foliage lower surface: Slightly darker than 147B. Venation, upper surface: 147A. Venation, lower surface: 147B. Petiole length: About 1.1 cm. Petiole diameter: About 2 mm. Petiole color, both surfaces: Close to 147B.

Inflorescence description:

*Appearance.*—Decorative-type inflorescence form with elongated oblong-shaped ray florets. Inflorescences borne on terminals above foliage, arising from leaf axils. Disk and ray florets arranged acropetally on a capitulum. About 5 to 6 inflorescences per lateral.

*Flowering response.*—Under natural season conditions, plants flower in early to mid-October in the Northern Hemisphere and continue to flower for at least three weeks depending on weather conditions.

*Inflorescence bud (before showing color).*—Height: About 5 mm. Diameter: About 7 mm. Phyllary color: 143A.

*Inflorescence size.*—Diameter: About 4.4 cm. Depth (height): About 1.5 cm. Disc diameter: About 3 mm or less, inconspicuous. Receptacle diameter: About 5.5 mm.

*Ray florets.*—Shape: Elongated oblong. Length: About 2 cm. Corolla tube length: About 5 mm. Width: About 7 mm. Apex: Mostly emarginate or rounded. Margin: Entire. Texture: Smooth, glabrous, satiny. Surface: Concave to mostly flat. Orientation: Initially upright and incurved, then perpendicular to the peduncle. Number of ray florets per inflorescence: About 292. Color: When opening, upper and lower surfaces: Darker than 77A. Opened inflorescence, upper surface: Close to 77A to 78A; fading to 78B to 78C with subsequent development. Opened inflorescence, lower surface: White, close to 155D, underlain with 77A to 77B.

*Disc florets.*—Shape: Tubular, apex dentate. Length: About 5 mm. Width: Apex: About 1.5 mm. Base: About 1 mm. Number of disc florets per inflorescence: Less than 10. Color: Immature: 154A to 9A. Mature: Apex: 9A to 12A. Mid-section: 154D. Base: 155D.

*Peduncle.*—Aspect: Flexible, angled about 45° from the stem. Length: First peduncle: About 4.6 cm. Fourth peduncle: About 5.9 cm. Diameter: About 2 mm. Texture: Pubescent. Color: 144A to 146A.

*Reproductive organs.*—Androecium: Present on disc florets only. Anther color: 12A. Pollen: Moderate. Pollen color: 14A. Gynoecium: Present on both ray and disc florets.

*Seed.*—Seed production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 40° C.

It is claimed:

1. A new and distinct cultivar of Chrysanthemum plant named 'Regal Yocheryl', as illustrated and described.

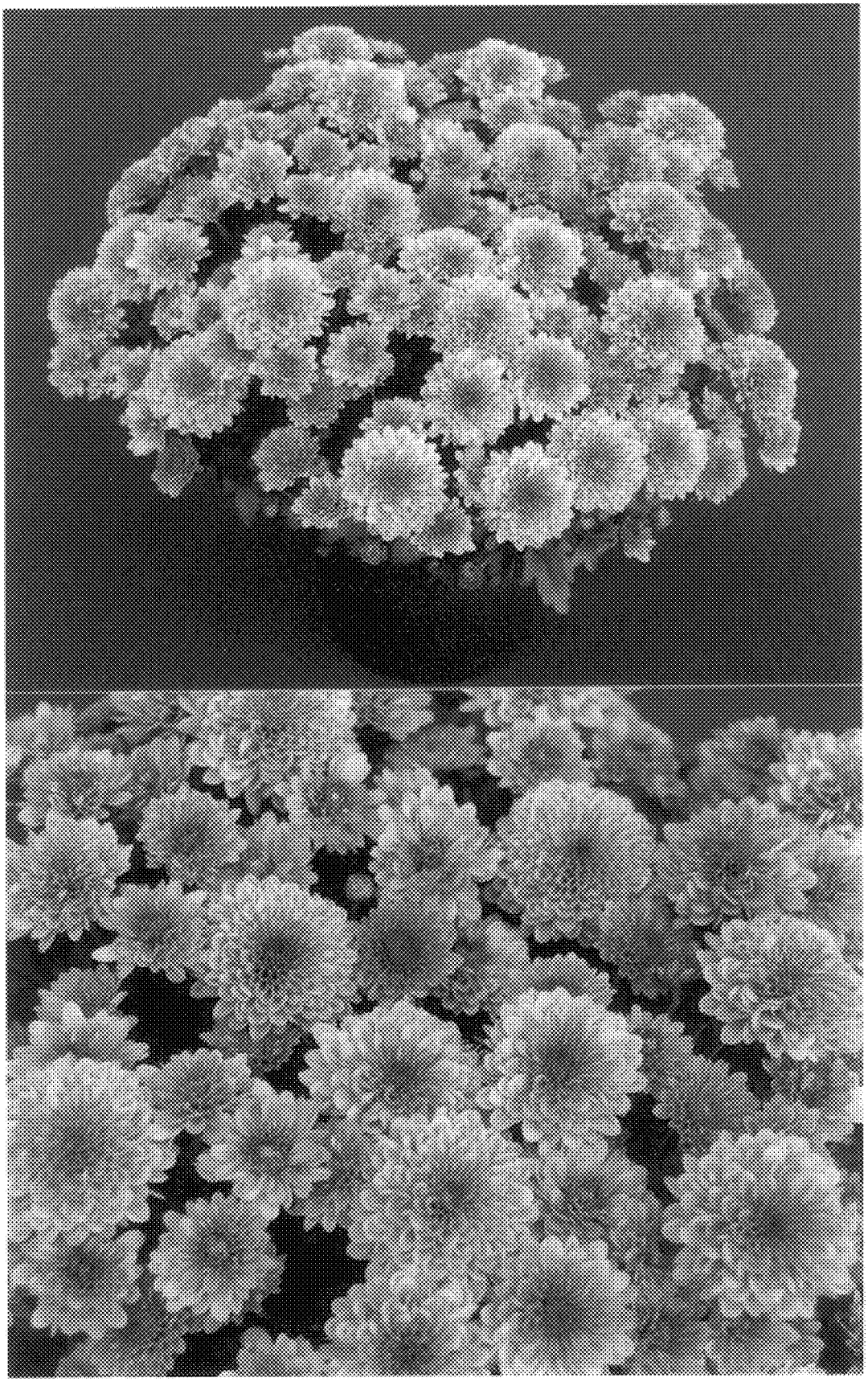

* * * * *